(12) United States Patent
Imura et al.

(10) Patent No.: US 9,321,708 B2
(45) Date of Patent: Apr. 26, 2016

(54) METHOD FOR PURIFYING (E)-1-CHLORO-3,3,3-TRIFLUOROPROPENE

(71) Applicant: Central Glass Company, Limited, Ube-shi, Yamaguchi (JP)

(72) Inventors: Hideaki Imura, Saitama (JP); Naoto Takada, Saitama (JP); Masamune Okamoto, Fujimino (JP)

(73) Assignee: Central Glass Company, Limited, Ube-shi (JP)

(*) Notice: Subject to any disclaimer, the term of this patent is extended or adjusted under 35 U.S.C. 154(b) by 0 days.

(21) Appl. No.: 14/375,193

(22) PCT Filed: Jan. 24, 2013

(86) PCT No.: PCT/JP2013/051402
§ 371 (c)(1),
(2) Date: Jul. 29, 2014

(87) PCT Pub. No.: WO2013/115048
PCT Pub. Date: Aug. 8, 2013

(65) Prior Publication Data
US 2015/0011803 A1    Jan. 8, 2015

(30) Foreign Application Priority Data

Feb. 2, 2012   (JP) ................. 2012-020458

(51) Int. Cl.
*C07C 17/389* (2006.01)
*C07C 19/08* (2006.01)
*C07C 21/18* (2006.01)
(Continued)

(52) U.S. Cl.
CPC ............. *C07C 17/389* (2013.01); *B01J 20/165* (2013.01); *B01J 20/18* (2013.01); *C07C 19/08* (2013.01); *C07C 21/18* (2013.01); *B01J 2220/42* (2013.01)

(58) Field of Classification Search
CPC .................................................. C07C 17/389
See application file for complete search history.

(56) References Cited

U.S. PATENT DOCUMENTS

| 6,018,084 | A  | 1/2000 | Nakada et al. |
| 6,844,475 | B1 | 1/2005 | Tung et al. |

(Continued)

FOREIGN PATENT DOCUMENTS

| CN | 1827566   | A | * | 9/2006 |
| CN | 101768046 | A | * | 7/2010 |

(Continued)

OTHER PUBLICATIONS

Zhang, B. et al. Journal of Fluorine Chemistry 2010, 131, pp. 554-560.*

(Continued)

Primary Examiner — Jafar Parsa
Assistant Examiner — Medhanit Bahta
(74) Attorney, Agent, or Firm — Crowell & Moring LLP

(57) ABSTRACT

Provided is a purification method for efficiently reducing an undesirable organic compound or compound in (E)-1-chloro-3,3,3-trifluoropropene and thereby obtaining (E)-1-chloro-3,3,3-trifluoropropene with high purity. The purification method of OF-1233E according to the present invention is characterized by bringing a composition containing OF-1233E and at least one organic compound selected from the group consisting of HCFC-142 isomers, HCFC-244fa, HFC-245fa, OF-1234E, OF-1234Z and OF-1233Z into contact with a solid adsorbent.

16 Claims, 1 Drawing Sheet

(51) Int. Cl.
  *B01J 20/18* (2006.01)
  *B01J 20/16* (2006.01)

(56) References Cited

U.S. PATENT DOCUMENTS

| | | | |
|---|---|---|---|
| 7,183,448 B2 | 2/2007 | Nakada et al. | |
| 8,217,208 B2 | 7/2012 | Hulse et al. | |
| 8,426,656 B2 | 4/2013 | Merkel et al. | |
| 8,487,144 B2 | 7/2013 | Hamasaki et al. | |
| 8,642,819 B2 | 2/2014 | Elsheikh et al. | |
| 2005/0033097 A1 | 2/2005 | Tung et al. | |
| 2005/0085674 A1 | 4/2005 | Nakada et al. | |
| 2010/0152504 A1 | 6/2010 | Hulse et al. | |
| 2010/0181186 A1* | 7/2010 | Uenveren | C07C 17/395 204/157.48 |
| 2011/0009678 A1 | 1/2011 | Bonnet et al. | |
| 2011/0172470 A1 | 7/2011 | Hamasaki et al. | |
| 2011/0201853 A1* | 8/2011 | Tung et al. | 570/168 |
| 2011/0218370 A1 | 9/2011 | Elsheikh et al. | |
| 2011/0245549 A1 | 10/2011 | Merkel et al. | |
| 2014/0051896 A1 | 2/2014 | Imura et al. | |

FOREIGN PATENT DOCUMENTS

| | | |
|---|---|---|
| JP | 9-183740 A | 7/1997 |
| JP | 09-241189 | 9/1997 |
| JP | 11-180908 A | 7/1999 |
| JP | 2000-229894 A | 8/2000 |
| JP | 2002-47218 A | 2/2002 |
| JP | 2002226411 A * | 8/2002 |
| JP | 2003-533447 | 11/2003 |
| JP | 2010-64990 A | 3/2010 |
| JP | 2010-531925 | 9/2010 |
| JP | 2010-533678 | 10/2010 |
| JP | 2012-509324 | 4/2012 |
| JP | 2013-510869 | 3/2013 |
| JP | 2013-523812 | 6/2013 |
| JP | 2014-534181 | 12/2014 |
| WO | WO 00/29361 A1 | 5/2000 |
| WO | WO 2005/014512 A2 | 2/2005 |
| WO | WO 2010/059496 A1 | 5/2010 |
| WO | WO 2011045559 A1 * | 4/2011 |
| WO | WO 2011/126692 A2 | 10/2011 |

OTHER PUBLICATIONS

JP 2002226411 A, 2002, pp. 1-4; English translation.*
CN 101768046 A, 2010, pp. 1-6; English translation.*
Zhang, B. et al. Publication No. CN1827566; Published Sep. 6, 2006, pp. 1-4; English translation.*
JPH09241189, 09-1197, pp. 1-6; English translation.*
International Search Report dated Apr. 16, 2013 with English translation (three (3) pages).
Japanese-language Written Opinion (PCT/ISA/237) dated Apr. 16, 2013.
Co-pending U.S. Appl. No. 13/929,261, filed Jun. 27, 2013.
European Extended Search Report dated Jul. 20, 2015 (Six (6) pages).
Japanese Office Action issued in counterpart Japanese Application No. 2012-020458 dated Oct. 20, 2015 (three (3) pages).

* cited by examiner

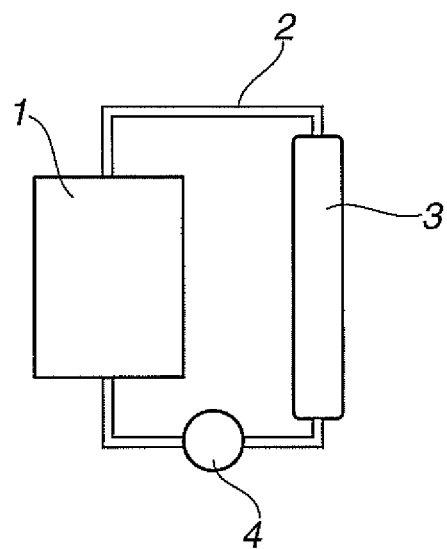

METHOD FOR PURIFYING (E)-1-CHLORO-3,3,3-TRIFLUOROPROPENE

FIELD OF THE INVENTION

The present invention relates to a method for purifying (E)-1-chloro-3,3,3-trifluoropropene (trans-1-chloro-3,3,3-trifluoropropene; also referred to as "OF-1233E" or "1233E").

BACKGROUND ART

It is known that 1233E is a fluoroolefin useful for working fluids, blowing agents, solvents, pharmaceutical and agrichemical intermediate products etc. For production of 1233E, there are disclosed a process for forming 1-chloro-3,3,3-trifluoropropene by reaction of 1,1,1,3,3-pentachloropropane (HCC-240fa) with hydrogen fluoride in a gas phase (Patent Document 1) and a process for forming 1,1,1-trifluoro-3-chloro-2-propene (1-chloro-3,3,3-trifluoropropene) by reaction of HCC-240fa with hydrogen fluoride in the absence of a catalyst (Patent Document 2). There is also disclosed in Patent Document 3 a process of reacting HCC-240fa in a liquid phase at a temperature lower than 150° C. in the presence of a Lewis acid catalyst or a mixture thereof within a reaction vessel, continuously extracting hydrogen chloride and 1-chloro-3,3,3-trifluoropropene as a reaction product from the reaction vessel, and then, isolating the 1-chloro-3,3,3-trifluoropropene from the extracted reaction product.

Since 1233E is obtained in the form of a mixture with a cis isomer, Patent Document 4 discloses a process for converting cis-1-chloro-3,3,3-trifluoropropene (1233Z) to trans-1-chloro-3,3,3-trifluoropropene (1233E). Further, Patent Document 5 discloses a process for forming 1233E by contact reaction of 1,1,1,3,3-pentafluoropropane (HFC-245fa) with hydrogen chloride on a catalyst.

On the other hand, it is known that solid adsorbents such as zeolite and alumina are capable of reducing hydrogen fluoride and alcohols in fluorinated unsaturated hydrocarbons (Patent Documents 6 and 7).

PRIOR ART DOCUMENTS

Patent Documents

Patent Document 1: Japanese Laid-Open Patent Publication No. H09-183740
Patent Document 2: Japanese Laid-Open Patent Publication No. H11-180908
Patent Document 3: International Publication No. WO 05/014512 A1
Patent Document 4: U.S. Patent Application Publication No. 2010/0152504
Patent Document 5: Japanese Laid-Open Patent Publication No. 2010-064990
Patent Document 6: Japanese Laid-Open Patent Publication No. 2002-047218
Patent Document 7: Japanese Laid-Open Patent Publication No. 2000-229894
Patent Document 8: International Publication No. WO 00/029361 A1

SUMMARY OF THE INVENTION

Problems to be Solved by the Invention

It is required to obtain 1233E as a high purity product for use as working fluids, blowing agents, solvents and pharmaceutical and agrichemical intermediate products. Due to the presence of a double bond, 1233E has a shorter atmospheric lifetime than those of conventional CFC (chlorofluorocarbon), HCFC (hydrochlorofluorocarbon) and HFC (hydrofluorocarbon) compounds and causes less environmental influences such as global warming and ozone layer depletion. The mixing of double-bond-free HFC compounds etc. into 1233E is thus not desired. Among others, saturated HCFC compounds each having both of chlorine and fluorine atoms are causative agents of not only global warming but also ozone layer depletion and regarded as particularly undesirable impurities. The mixing of highly-reactive olefin compounds other than 1233E is not also desired.

In the reaction processes of Patent Documents 1 to 5, however, 1233E is obtained in the form of a reaction mixture with various organic compounds such as isomer compound, i.e., (Z)-1-chloro-3,3,3-trifluoropropene (cis-1-chloro-3,3,3-trifluoropropene; also referred to as "OF-1233Z" or "1233Z") and excessively fluorinated compounds, e.g., 1,1,1,3,3-pentafluoropropane (also referred to as "HFC-245fa" or "245fa"), 1-chloro-1,3,3,3-tetrafluoropropane (also referred to as "HCFC-244fa" or "244fa"), saturated compounds of the formula $C_2H_3ClF_2$ (each also referred to as "HCFC-142 isomer" or "142"), (E)-1,3,3,3-tetrafluoropropene (also referred to as "OF-1234E" or "1234E") and (Z)-1,3,3,3-tetrafluoropropene (also referred to as "OF-1234Z" or "1234Z"). Herein, examples of the 142 isomer include $CHF_2CH_2Cl$ (35° C.), $CH_3CCl_2F$ (−9° C.), $CH_2FCHClF$ and $CH_2ClCHClF$.

In general, distillation is an easy technique to obtain high-purity 1233E from the reaction mixture. The distillation yield of 1233E is however low since the boiling point of 1233E is close to the boiling points of the organic compounds other than 1233E in the reaction mixture (see Scheme 1). In particular, it is known that 245fa and 1233E are azeotropic with each other (See Patent Document 8) so that the separation of 245fa and 1233E by distillation is not efficient.

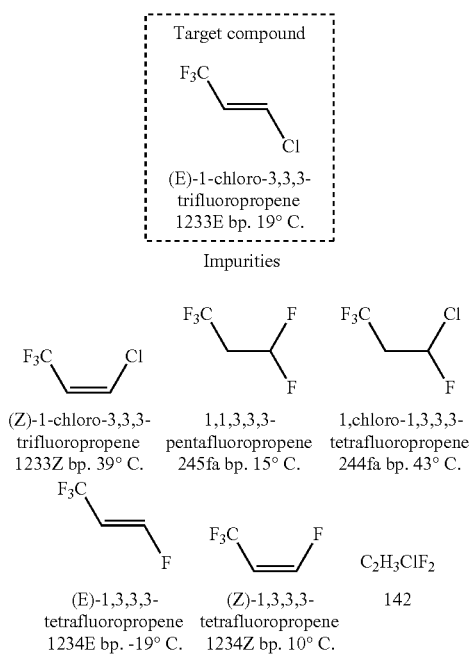

Scheme 1

It is accordingly an object of the present invention to provide a method for obtaining high-purity 1233E. In other words, it is an object of the present invention to provide a method for efficiently reducing, in a crude 1233E containing an organic compound such as 142, 244fa, 245fa, 1234E, 1234Z and/or 1233Z as an undesired impurity, the undesired organic compound. Hereinafter, the undesirable impurity such as 142, 244fa, 245fa, 1234E, 1234Z or 1233Z is also simply referred to as "impurities".

Means for Solving the Problems

In view of the above problems, the present inventors have made extensive researches and consequently found that, although 142, 244fa, 245fa, 1234E, 1234Z and 1233Z are difficult to separate from 1233E, it is possible by contact of 1233E containing any of these impurities with a solid adsorbent to efficiently reduce the impurity in 1233E. The present inventors have also found that, among various kinds of solid adsorbents, silica-alumina compounds are effective; zeolites and allophanes are more effective; and X-type zeolites are especially effective.

Namely, the present invention includes the following aspects.

Inventive Aspect 1

A method for purifying OF-1233E, comprising bringing a composition containing OF-1233E and at least one organic compound selected from the group consisting of HCFC-142 isomers, HCFC-244fa, HFC-245fa, OF-1234E, OF-1234Z and OF-1233Z into contact with a solid adsorbent.

Inventive Aspect 2

The method according to Inventive Aspect 1, wherein the composition containing OF-1233E and HFC-245fa is brought into contact with the solid adsorbent.

Inventive Aspect 3

The method according to Inventive Aspect 1 or 2, wherein the solid adsorbent is a zeolite.

Inventive Aspect 4

The method according to Inventive Aspect 3, wherein the zeolite is an X-type zeolite.

Inventive Aspect 5

A solid-liquid heterogeneous mixture for use in the method according to any one of Inventive Aspects 1 to 4, comprising:
a composition containing OF-1233E and at least one organic compound selected from the group consisting of HCFC-142 isomers, HCFC-244fa, HFC-245fa, OF-1234E, OF-1234Z and OF-1233Z; and
a solid adsorbent.

In the present invention, the reduction of an undesired organic compound means that the content of at least one organic compound selected from the group consisting of 142, 244fa, 245fa, 1234E, 1234Z and 1233Z is reduced by 100 ppm or more before and after contact with a solid adsorbent or means, in the case where the content of the at least one organic compound is 100 ppm or less before the contact, the content of the at least one organic compound is reduced to 10 ppm or less after the contact as measured by the after-mentioned gas chromatography analysis. There is substantially no influence on the physical properties and environmental safety of 1233E when the content of the at least one organic compound in 1233E is 10 ppm or less. It is preferable that the amount of reduction of the organic compound is as large as possible; and the kind of the organic compounds reduced is as many as possible. It is particularly preferable to reduce 142 and 244fa that have influences on both of ozone layer depletion and global warming, and to reduce 245fa that forms an azeotropic mixture with 1233E.

It is possible according to the present invention to reduce the undesired organic compound in the crude 1233E with simple operation and purify the 1233E to a high purity level. It is also possible to, after purifying 1233E by distillation, further purify the distillation purification product to a higher purity level.

BRIEF DESCRIPTION OF THE DRAWINGS

FIG. 1 is a schematic view showing a circulation purification system according to one embodiment of the present invention.

DESCRIPTION OF THE EMBODIMENTS

As mentioned above, the purification method of the present invention includes bringing a composition containing OF-1233E and at least one organic compound selected from the group consisting of HCFC-142 isomers, HCFC-244fa, HFC-245fa, OF-1234E, OF-1234Z and OF-1233Z (hereinafter also referred to as "crude 1233E") into contact with a solid adsorbent.

The purification method of the present invention is applicable to the crude 1233E regardless of how the crude 1233E is obtained. There is no particular limitation on the component ratio of the crude 1233E.

For example, the crude 1233E can be a reaction product obtained by reaction of HCC-240fa with hydrogen fluoride, a reaction mixture obtained by isomerization of 1233Z or a product obtained by reaction of 245fa with hydrogen chloride on a catalyst.

The crude 1233E may be one obtained by subjecting the above reaction mixture to any known purification treatment. As the purification treatment, it is feasible to adopt washing with water or liquid, drying, ordinary distillation, extractive distillation etc. The crude 1233E, which has been recovered after use as a solvent, detergent, flux, cooling medium, heat medium, working fluid or blowing agent, etc. and contains 142, 244fa, 245fa, 1234E, 1234Z and/or 1233Z, can also be treated by the purification method of the present invention. In other words, the purification method of the present invention is useful for recycling of the used 1233E product.

In such a case, the content of 1233E in the crude 1233E is 80 to 99.9%; and the total content of the above impurities and the other impurities in the crude 1233E is 0.01 to 20%. It is preferable that the total content of the impurities is as low as possible. In general, the total content of the impurities is preferably 0.01 to 10%.

Any of the above impurities, and/or any other component or components, may be added to the crude 1233E as desired by a person skilled in the art. In this case, it is preferable that: the concentration of 1233E is 70% or more; and the total content of the impurities is 10% or less although the component ratio of the crude 1233E is arbitrary.

There is no particular limitation on the content of each of the organic compounds in the crude 1233E. Even when the content of 1233E is about 20%, the total content of 142, 244fa, 245fa, 1234E, 1234Z and 1233Z is about 0.1%, the purification method of the present invention is applicable to the crude 1233E as long as the remaining 79.9% is a solvent or high-boiling-point component separable by distillation. In this case, it is feasible to obtain high-purity 1233E by distillation after reducing the impurities by the solid adsorbent.

It is known that 1233E and 245fa forms an azeotropic mixture at a ratio of 35:65 (see Patent Document 8). Further, 1234E, 1234Z and 1233Z are very similar in structure to 1233E and each have a boiling point close to that of 1233E so that it is difficult to separate 1234E, 1234Z and 1233Z from 1233E by distillation (see Example 10). When the crude 1233E containing a large amount of these compounds is subjected to distillation, the yield of distillation is lowered. Further, it is substantially impossible to completely separate these compounds by a distillation column with less number of plates. It is thus effective to purify the main distillation fraction to a higher purity level by the present invention. Moreover, it is feasible to purify a commercially available 1233E to a higher purity level by the present invention.

In the present invention, there can be used a zeolite, clay, alumina, silica, silica-alumina, activated carbon or a complex or mixture thereof as the solid adsorbent. Among others, a zeolite, that is, a porous silica-alumina adsorbent is preferably usable.

There is no particular limitation on the kind of the alumina. The alumina can be amorphous, crystalline or hydrated. Among others, preferred is low-crystalline silica. Specific examples of the alumina are those available for catalysts (e.g. under the trade name of N612N from Nikki Chemicals Co. Ltd.)

There is no particular limitation on the kind of the silica. The silica can be amorphous, crystalline or hydrated. A silica gel or diatomaceous earth is usable. Specific examples of the silica are those available under the trade names of CARiACT and Q-15 (each from Fuji Davison Co., Ltd.) etc. There can also effectively be used allophane, which is a silica-alumina mineral, as the solid adsorbent.

There is also no particular limitation on the kind of the activated carbon. A plant-based, lime-based or petroleum-based activated carbon is usable. Suitable examples of the activated carbon are plant-based activated carbons prepared from wood, wood charcoal, coconut shell charcoal etc. and lime-based activated carbons prepared from bituminous coal, lignite etc.

The zeolite is defined, according to International Zeolite Association, as "a compound having a composition ABn (n≈2), where A has four bonds; and B has two bonds, to form an open three-dimensional network structure with a framework density of 20.5 or less".

According to International Mineralogical Association, the zeolite is defined as follows: "the zeolite is a crystalline substance characterized by a framework structure having tetrahedrons, in each of which four oxygen atoms are coordinated to a cation, linked together; the framework structure has pores formed of channels and holes and open to the outside so as to allow passage of gest molecules; the channels and the holes are normally occupied by molecules and exchangeable cations; and the framework structure may become discontinuous when OH group or F group occupies one of oxygen atoms on apexes of the tetrahedrons".

In the present invention, the zeolite can be of the type defined by International Zeolite Association or by International Mineralogical Association. The zeolite is sometimes called "boiling bubble stone" or "boiling stone".

Among various kinds of zeolites, aluminosilicate-type zeolites are preferred. Namely, the zeolite is preferably of the type having a basic skeleton formed of Si, Al, O and H and containing an alkali or alkali-earth metal such as Li, Na, K or Ca. In the case where the zeolite is natural, any other metal may be contained in the zeolite. In the case where the zeolite is synthetic, any metal other than the above metal may be doped into the zeolite as desired.

There is no particular limitation on the kind of the zeolite. The zeolite can be of faujasite series, chabazite series or mordenite series. Examples of the faujasite series zeolite are: natural zeolites such as faujasite; and synthetic zeolites exemplified by A-type zeolites such as zeolites 3A, 4A and 5A, X-type zeolites such as zeolites 10X and 13X and Y-type zeolites. Examples of the chabazite series zeolite are: natural zeolites such as chabazite, gmelinite, erionite and levynite; and synthetic zeolites such as zeolites R, S and T. Examples of the mordenite zeolite are natural or synthetic zeolites such as mordenite, clinoptilolite, etc.

Regardless of whether the zeolite is natural or synthetic, it is feasible to use the zeolite after modifying the zeolite by baking, acid contact, base contact or ion exchange, etc. The ion suitable for the ion exchange is an ion of alkali metal or an ion of alkali earth metal. The alkali metal ion can be, for example, lithium ion, sodium ion, potassium ion, rubidium ion or cesium ion. The alkali earth metal ion can be, for example, beryllium ion, magnesium ion, calcium ion, strontium ion or barium ion.

In the case of the synthetic zeolite, the pore distribution, the Si/Al ratio and the contents of other metals can be changed as desired by a person skilled in the art. In general, synthetic zeolites are more stable in quality than natural zeolites. Readily available synthetic zeolites such as A-, X- and Y-type zeolites are preferred. More preferred are K-exchanged A-type zeolite (sometimes referred to as "MS-3A", "KA" or "Molecular Sieve 3A"), Na-exchanged A-type zeolite (sometimes referred to as "MS-4A", "NaA" or "Molecular Sieve 4A"), Ca-exchanged A-type zeolite (sometimes referred to as "MS-5A", "CaA" or "Molecular Sieve 5A"), Ca-exchanged X-type zeolite (sometimes referred to as "MS-10X", "CaX" or "Molecular Sieve 10X"), and Na-exchanged X-type zeolite (sometimes referred to as "MS-13X", "NaX" or "Molecular Sieve 13X"). Among others, Na- and Ca-exchanged X-type zeolites are particularly preferred since each of these zeolites are effective for all of the impurity compounds.

In the present invention, the zeolite can be in any form such as powder form, granule form or granulated form. In the case of using the zeolite in a packed column, it is preferable that the zeolite is spherical or rod-shaped in view of ease of handling.

There is no particular limitation on the technique of contact between the crude 1233E and the solid adsorbent. It is feasible to adopt a batch system in which the solid adsorbent is added to the crude 1233E in a container so that the crude 1233E and the solid adsorbent are brought into contact with each other for a predetermined time with or without stirring, or a flow system in which the crude 1233E is allowed to flow through container (also referred to as "adsorption column") filled with the solid adsorbent. It is also feasible in the flow system to circulate the crude 1233E (circulation system). In the case of packing the column with the solid adsorbent and allowing the crude 1233E to flow through the packed column, the solid adsorbent is preferably in the form of beads or pellets, which cause less pressure loss. One example of the circulation system is to feed a liquid of the crude 1233E from a tank 1 through a line 2 to an adsorption column 3 packed with the solid adsorbent and circulate the crude 1233E by a pump 4 as shown in FIG. 1.

The crude 1233E can be either in gas form or liquid form at the time of contact with the solid adsorbent. In view of high productivity, it is preferable to bring the crude 1233E in liquid form into contact with the solid absorbent.

The time required for adsorption treatment in the batch system varies depending on the adsorption temperature, the initial and target concentrations of the impurities, the diffusion state, the kind and state of the solid adsorbent, the weight ratio of the solid adsorbent and 1233E. The adsorption treatment time is generally in the range of 5 minutes to 48 hours, preferably 30 minutes to 6 hours, more preferably 60 minutes to 3 hours. If the treatment time is short, the impurity concentration may not be lowered sufficiently. There is a tendency that, after the impurity concentration is abruptly lowered at the initial stage of adsorption, the rate of lowering of the impurity concentration decreases with time. Thus, the adsorption treatment results in deterioration of productivity even if the treatment time is set excessively long.

The weight ratio of the 1233E and the solid adsorbent in the batch system varies depending on the adsorption temperature, the initial and target concentrations of the impurities, the diffusion state and the kind and state of the solid adsorbent. In common sense, the weight ratio of the crude 1233E/the solid adsorbent is preferably in the range of 1 to 30.

There is no particular limitation on the adsorption temperature. The adsorption temperature is preferably −50 to 30° C., more preferably −20 to 10° C. If the adsorption temperature is higher than the above range, there may occur an unexpected decomposition reaction. There may also occur an increase of pressure under high-temperature conditions due to the fact that the boiling point of 1233E is 19° C. It is economically unfavorable to perform the adsorption treatment under cooling conditions lower than −50° C. because such cooling requires special cooling equipment and results in increases of equipment cost and operation cost.

There is no particular limitation on the adsorption pressure in either of the batch system or the flow system. Although it is easy to perform the adsorption treatment at around normal atmospheric pressure, the adsorption treatment can be performed under pressurized conditions by the use of a pump or nitrogen. It is an industrially common technique to feed the crude 1233E in liquid form into the adsorption column by a pump. In such pressure feeding, the 1233E can be pressurized to an arbitrary pressure. However, there arises a need for expensive pressure-proof equipment if the pressurization is performed to an excessively high level. The adsorption pressure is thus generally preferably in the range of −0.05 to +1.0 MPa.

In the flow system, the adsorption treatment conditions varies depending on the number of flows, the kind and state of the solid adsorbent, the amount of the solid adsorbent packed, the dimensions (inner diameter and length) of the adsorption column, the treatment temperature and the flow rate. As the dimensions of the adsorption column, the length/inner diameter ratio of the adsorption column is generally in the range of 3 to 200, preferably 4 to 50. The impurities may not be reduced sufficiently if the length/inner diameter ratio is small. If the length/inner diameter ratio is excessively large, there arises a need for expensive equipment due to the occurrence of a large pressure loss. When the number of flows is one, for example, the retention time is preferably about 1 minute to 120 minutes. Further, the liquid flow linear velocity (void column linear velocity) is about 1 cm/hr to 10 m/hr, preferably 2 cm/hr to 5 m/hr. If the linear velocity is slower than 1 cm/hr, the treatment time becomes so long that the adsorption treatment unfavorably results in deterioration of productivity. The impurities may be reduced sufficiently if the linear velocity exceeds 10 m/hr.

Herein, the state of the solid adsorbent refers to how much impurities have been adsorbed on the solid adsorbent. When the solid adsorbent is in a fresh state, both of the adsorption capacity and adsorption rate of the solid adsorbent are large. The adsorption capacity and adsorption rate of the solid adsorbent are naturally lowered in the state where the impurities are adsorbed in a large amount on the solid adsorbent. In such a case, it is feasible to regenerate the solid adsorbent by desorption treatment. For example, the solid adsorbent can be regenerated by removing the liquid in the adsorption column and then reducing the pressure inside the adsorption column. After the pressure reduction, heating may optionally be conducted. In the case of conducting heating after the pressure reduction, the heating temperature is preferably 30 to 300° C. It is also feasible to obtain a concentrate of the impurities that have been adsorbed on the solid adsorbent by cooling and collecting the desorpted gas component during the desorption treatment.

Depending on the desire of a person skilled in the art, the crude 1233E and the solid adsorbent can be introduced into a storing/transporting container and thereby stored and transported in the form of a solid-liquid heterogeneous mixture. In the case of storing, transporting and selling the crude 1233E by means of a stainless steel container, for example, it is feasible by adding the solid adsorbent to the crude 1233E in the container to provide the crude 1233E in which the undesirable impurities are reduced during the storing etc. The weight ratio of the crude 1233E and the solid adsorbent varies depending on the style of embodiment and the bulk density of the solid adsorbent and thus can be set as appropriate. In general, the weight ratio of the crude 1233E/the solid adsorbent is preferably in the range of 0.1 to 200, more preferably 1 to 100. In the case of the solid-liquid heterogeneous mixture, the weight ratio of the crude 1233E/the solid adsorbent is preferably in the range of 5 to 50, more preferably 8 to 40. If the weight ratio is less than 5, there occurs unfavorable problems that: the solid adsorbent needs to be used in an excessive amount; and the amount of 1233E stored in the container becomes small. If the weight ratio exceeds 50, a sufficient adsorption effect may not be obtained.

In the case of storing and transporting the solid-liquid heterogeneous mixture in the container, it is preferable to keep the solid-liquid heterogeneous mixture under low-temperature, low-humidity conditions. More specifically, the temperature is in the range of −50 to 25° C., preferably −20 to 5° C. If the temperature is higher than 25° C., there may occur degeneration of 1233E and the impurities depending on the length of the storing period. It is thus not economical to set the temperature lower than −50° C. If the humidity is high, there may occur unfavorable problems that: the metal container may be corroded by humidity; and water enters the container during opening/closing of the container.

Even in the flow system, it is feasible to purify the crude 1233E to a high purity by stopping the flow of the crude 1233E, allowing the crude 1233E to stay in the adsorption column and thereby storing the crude 1233E and the solid adsorbent as the solid-liquid, heterogeneous mixture. In this case, the weight ratio of the crude 1234zeE/the solid adsorbent is preferably in the range of 0.1 to 3 although there is no particular limitation on the weight ratio of the crude 1234zeE/the solid adsorbent.

EXAMPLES

The present invention will be described in more detail below by way of the following examples. The following examples are however illustrative only and are not intended to limit the present invention thereto. It is herein noted that, unless otherwise specified, the unit "%" of organic composition analysis values means "area %" as measured by gas chromatography with FID.

Example 1

Purification in Batch System

First, 50 g of solid adsorbent "Secard KW" (main component: allophane) available from Shinagawa Chemicals Co., Ltd. was placed in a 250-cc high-density polyethylene container. The container was cooled to −10° C. Into this container, added was 150 g of crude 1233E that had been cooled to −10° C. The container was then left still in a refrigerator of −20° C. for 24 hours. After that, a liquid fraction was sampled from the container and analyzed by gas chromatography (FID).

Examples 2 to 7

The same experimental tests as in Example 1 were performed using different kinds of solid adsorbents.

The gas chromatography profiles of Examples 1 to 7 are shown in TABLE 1. (In TABLE 1, the value "0.0000" means "not detected".)

TABLE 1

|  | 1234E (%) | 245fa (%) | 1234Z (%) | 1233E (%) | $C_2H_3ClF_2$ (%) | 244fa (%) | 1233Z (%) | Others (%) |
|---|---|---|---|---|---|---|---|---|
| Before adsorption treatment (crude 1233E) | 4.0894 | 0.4786 | 0.6275 | 90.7114 | 0.0515 | 0.2336 | 2.6653 | 1.1427 |
| Example 1 Allophane | 3.8049 | 0.3647 | 0.4812 | 91.8210 | 0.0110 | 0.1681 | 2.1876 | 1.1615 |
| Example 2 Zeolite A-1 | 4.0812 | 0.3511 | 0.5939 | 90.0973 | 0.0035 | 0.2321 | 2.7003 | 1.9406 |
| Example 3 Zeolite A-2 | 4.0762 | 0.3474 | 0.5943 | 90.1989 | 0.0034 | 0.2335 | 2.6978 | 1.8485 |
| Example 4 Zeolite A-3 | 4.0115 | 0.3328 | 0.5804 | 90.2866 | 0.0036 | 0.2442 | 2.7066 | 1.8343 |
| Example 5 Zeolite X-1 | 2.3678 | 0.0007 | 0.0092 | 96.4636 | 0.0000 | 0.0000 | 0.0564 | 1.1023 |
| Example 6 Zeolite X-2 | 2.7825 | 0.0010 | 0.0166 | 95.9037 | 0.0000 | 0.0007 | 0.1220 | 1.1735 |
| Example 7 Activated carbon | 4.2846 | 0.5375 | 0.6524 | 90.6915 | 0.0459 | 0.2296 | 2.3365 | 1.2220 |

Allophane: Secard KW, granule form (0.5 to 3 mm), available from Shinagawa Chemicals Co., Ltd.
Zeolite A-1: Molecular Sieve 3A, pellet (1/16), available from Wako Pure Chemical Industries, Ltd.
Zeolite A-2: Molecular Sieve 4A, pellet (1/16), available from Wako Pure Chemical Industries, Ltd.
Zeolite A-3: Molecular Sieve 5A, pellet (1/16), available from Wako Pure Chemical Industries, Ltd.
Zeolite X-1: Molecular Sieve 13X, pellet (1/16), available from Wako Pure Chemical Industries, Ltd.
Zeolite X-2: Zeolite F-9, pellet (1.5 mmf), available from Wako Pure Chemical Industries, Ltd.
Activated carbon: Shirasagi G2X, cylindrical form (4-6 mesh), available from Takeda Pharmaceutical Company Limited All of the solid adsorbents used in Examples 1 to 7 had a removal effect on any of undesired impurities. In particular, there was seen reduction of ozone-destroying compound 142 in all of Examples 1 to 7. The X-type zeolites used in Examples 5 and 6 had a significant adsorption effect on all of undesired impurities.

Example 8

Purification in Flow System

A stainless steel adsorption column having an inner diameter of 10 mm and a length of 400 mm was packed with 14.9 g of Molecular Sieve 13X (the same product (new product) as used in Example 5) available from Wako Pure Chemical Industries, Ltd., followed by cooling the adsorption column in a large-sized (50-L) ice cooling bath (0 to 3° C.). Crude 1233E was cooled in the same ice cooling bath, pressurized by nitrogen and allowed to flow up through the adsorption column at a void column linear velocity of 183 cm/hr (3 g/min). At this time, the pressure inside the adsorption column was 0.2 MPa. The resulting composition was sampled at an outlet of the adsorption column and analyzed by gas chromatography. The test results are shown in TABLE 2. Even in the flow system, the solid adsorbent had an adsorption effect on undesired impurities as in the case of the batch systems of Examples 1 to 7.

TABLE 2

| Accumulated flow rate (g) | 1234E (%) | 245fa (%) | 1234Z (%) | 1233E (%) | Others (%) |
|---|---|---|---|---|---|
| Before flow treatment (crude 1233E) | 1.7464 | 0.3627 | 0.2953 | 97.5443 | 0.0513 |
| 100 | 1.3447 | 0.0093 | 0.0277 | 98.5744 | 0.0439 |
| 196 | 1.7076 | 0.0410 | 0.0953 | 98.1115 | 0.0446 |
| 267 | 1.5744 | 0.0393 | 0.1007 | 98.2416 | 0.0440 |
| 573 | 1.4851 | 0.1581 | 0.2377 | 98/0773 | 0.0418 |

Example 9

Desorption Treatment of Solid Adsorbent

After the completion of Example 8, the adsorption column was taken out of the ice cooling bath. The liquid was purged from the adsorption column by the flow of nitrogen. After stopping the flow of nitrogen, the adsorption column was vacuumed by a vacuum pump (room temperature). After 10 minutes of the vacuuming, the adsorption column was immersed in a water bath of 90° C. and kept vacuumed for 5 hours. By this, the solid adsorbent was regenerated. Using the thus-obtained solid adsorbent, the same experimental test as in Example 8 was performed. The test results are shown in TABLE 3. The solid adsorbent regenerated by the above desorption treatment had the same impurity removal effect as that of the new solid adsorbent used in Example 8. It has thus been confirmed that the solid adsorbent is regeneratable.

TABLE 3

| Accumulated flow rate (g) | 1234E (%) | 245fa (%) | 1234Z (%) | 1233E (%) | Others (%) |
|---|---|---|---|---|---|
| Before flow treatment | 1.7464 | 0.3627 | 0.2953 | 97.5443 | 0.0513 |
| 100 | 1.3266 | 0.0093 | 0.0311 | 98.5892 | 0.0438 |
| 200 | 1.7017 | 0.0409 | 0.1051 | 98.1082 | 0.0441 |

Example 10

The same experimental test as in Example 5 was performed using 1233E that had been purified to 99.9912% by a distillation column with 50 theoretical plates. As a result, the 1233E was obtained with an ultra high purity of 99.992% as shown in TABLE 4. Although 1234E, 245fa and 1234Z remained unremoved by the distillation, these impurities were not detected after the adsorption treatment. It has thus been confirmed that the purification method of the present invention is very effective for high purification of 1233E.

TABLE 4

| Accumulated flow rate (g) | 1234E (%) | 245fa (%) | 1234Z (%) | 1233E (%) | Others (%) |
|---|---|---|---|---|---|
| Before flow treatment | 0.0031 | 0.0011 | 0.0012 | 99.9912 | 0.0034 |
| After flow treatment | 0.0000 | 0.0000 | 0.0000 | 99.9992 | 0.0008 |

As described above, it is possible by the purification method according to the present invention to reduce the undesired organic compound in the crude 1233E with simple operation and purify the 1233E to a high purity level.

DESCRIPTION OF REFERENCE NUMERALS

1: Tank filled with crude 1233E
2: Line
3: Adsorption column filled with solid adsorbent
4: Liquid feeding pump

The invention claimed is:

1. A method for purifying (E)-1-chloro-3,3,3-trifluoropropene (OF-1233E), comprising bringing a composition containing OF-1233E and 1,1,1,3,3-pentafluoropropane (HCFC-245fa) into contact with a solid adsorbent,
wherein the solid adsorbent is a zeolite X; and
wherein the weight ratio of the composition to the solid adsorbent is in a range of 5 to 50.

2. The method according to claim 1, wherein the zeolite X is at least one of a Na-exchanged zeolite X and a Ca-exchanged zeolite X.

3. The method according to claim 1, wherein the weight ratio of the composition to the solid adsorbent is in the range of 8 to 40.

4. The method according to claim 2, wherein the weight ratio of the composition to the solid adsorbent is in the range of 8 to 40.

5. A method for purifying OF-1233E, comprising bringing a composition containing OF-1233E, HFC-245fa, and at least one organic compound selected from the group consisting of compounds of the formula $C_2H_3ClF_2$ (HCFC-142 isomers), 1-chloro-1,3,3,3-tetrafluoropropane (HCFC-244fa), (E)-1,3,3,3-tetrafluoropropene (OF-1234E), (Z)-1,3,3,3-tetrafluoropropene (OF-1234Z), and (Z)-1-chloro-3,3,3-trifluoropropene (OF-1233Z) into contact with a solid adsorbent,
wherein the solid adsorbent is a zeolite X; and
wherein the weight ratio of the composition to the solid adsorbent is in a range of 5 to 50.

6. The method according to claim 5, wherein the zeolite X is at least one of a Na-exchanged zeolite X and a Ca-exchanged zeolite X.

7. The method according to claim 5, wherein the weight ratio of the composition to the solid adsorbent is in the range of 8 to 40.

8. The method according to claim 6, wherein the weight ratio of the composition to the solid adsorbent is in the range of 8 to 40.

9. A solid-liquid heterogeneous mixture for use in the method according to claim 1, comprising:
a composition containing OF-1233E and; and
a solid adsorbent,
wherein the solid adsorbent is a zeolite X; and
wherein the weight ratio of the composition to the solid adsorbent is in a range of 5 to 50.

10. The solid-liquid heterogeneous mixture according to claim 9, wherein the zeolite X is at least one of a Na-exchanged zeolite X and a Ca-exchanged zeolite X.

11. The solid-liquid heterogeneous mixture according to claim 9, wherein the weight ratio of the composition to the solid adsorbent is in the range of 8 to 40.

12. The solid-liquid heterogeneous mixture according to claim 10, wherein the weight ratio of the composition to the solid adsorbent is in the range of 8 to 40.

13. The solid-liquid heterogeneous mixture for use in the method according to claim 5, comprising:
a composition containing OF-1233E, HFC-245fa, and at least one organic compound selected from the group consisting of HCFC-142 isomers, HCFC-244fa, OF-1234E, OF-1234Z, and OF-1233Z; and
a solid adsorbent,
wherein the solid adsorbent is a zeolite X; and
wherein the weight ratio of the composition to the solid adsorbent is in a range of 5 to 50.

14. The solid-liquid heterogeneous mixture according to claim 13, wherein the zeolite X is at least one of a Na-exchanged zeolite X and a Ca-exchanged zeolite X.

15. The solid-liquid heterogeneous mixture according to claim 13, wherein the weight ratio of the composition to the solid adsorbent is in the range of 8 to 40.

16. The solid-liquid heterogeneous mixture according to claim 14, wherein the weight ratio of the composition to the solid adsorbent is in the range of 8 to 40.

* * * * *